United States Patent
Roberts et al.

(10) Patent No.: US 9,405,493 B2
(45) Date of Patent: *Aug. 2, 2016

(54) PHARMACY PRINTER SYSTEM AND METHOD

(71) Applicant: INVENTIV HEALTH, INC., Burlington, MA (US)

(72) Inventors: Michael F. Roberts, Palm Harbor, FL (US); Simon Banfield, Tierra Verde, FL (US)

(73) Assignee: INVENTIV HEALTH, INC., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/709,016

(22) Filed: May 11, 2015

(65) Prior Publication Data

US 2015/0242171 A1 Aug. 27, 2015

Related U.S. Application Data

(60) Continuation of application No. 13/967,286, filed on Aug. 14, 2013, which is a division of application No. 13/229,651, filed on Sep. 9, 2011, now Pat. No. 8,531,714, which is a continuation of application No. 11/748,239, filed on May 14, 2007, now Pat. No. 8,072,635.

(60) Provisional application No. 60/822,880, filed on Aug. 18, 2006.

(51) Int. Cl.
*G06K 15/00* (2006.01)
*G06F 3/12* (2006.01)
(Continued)

(52) U.S. Cl.
CPC .......... *G06F 3/1243* (2013.01); *G06F 19/3456* (2013.01); *G06K 15/02* (2013.01); *G06K 15/1806* (2013.01); *G06K 15/1868* (2013.01); *G06Q 10/00* (2013.01); *G06Q 50/22* (2013.01)

(58) Field of Classification Search
CPC ... G06F 19/3456; G06F 3/1243; G06K 15/02; G06K 15/1806; G06K 15/1868; G06Q 10/00; G06Q 50/22
USPC ............ 358/1.1, 1.2, 1.4, 1.5, 1.9, 1.11, 1.12, 358/1.13, 1.14, 1.15, 1.16, 1.17, 1.18, 375
See application file for complete search history.

(56) References Cited

U.S. PATENT DOCUMENTS 6,112,182 A 8/2000 Akers et al.
6,202,923 B1 3/2001 Boyer et al.
(Continued)

OTHER PUBLICATIONS

International Searching Authority, Written Opinion, Mailed Dec. 26, 2007, 7 pages.
(Continued)

*Primary Examiner* — Thierry L Pham
(74) *Attorney, Agent, or Firm* — Kegler Brown Hill & Ritter Co. L.P.A.; James Pingor (57) ABSTRACT

A computer network system and method for printing accompanying information and prescription labels in pharmacies, comprises: a central CS; a PMS; a data transmission network through which said PMS and said central CS can communicate; wherein said PMS includes an I/O terminal, a scanner, and a first printer; wherein said PMS includes a PMS SO and a Catalina SO; said PMS SO is configured to receive and store prescription information for a prescription, and to associate a prescription identification with said prescription; said Catalina SO is configure to select accompanying information for said prescription, to format and save said accompanying information in an accompanying information print file; and said PMS is configured to print a prescription label for said prescription and said accompanying information print file.

18 Claims, 6 Drawing Sheets

(51) Int. Cl.

| | | |
|---|---|---|
| *G06Q 10/00* | (2012.01) | |
| *G06Q 50/22* | (2012.01) | |
| *G06F 19/00* | (2011.01) | |
| *G06K 15/02* | (2006.01) | |
| *G06F 15/00* | (2006.01) | |

(56) References Cited

U.S. PATENT DOCUMENTS

| | | |
|---|---|---|
| 6,260,761 B1 | 7/2001 | Peoples, Jr. |
| 6,301,013 B1 | 10/2001 | Momose et al. |
| 6,759,366 B2 | 7/2004 | Beckerdite et al. |
| 6,784,906 B2 | 8/2004 | Long et al. |
| 7,009,723 B1 | 3/2006 | Bartholet et al. |
| 2004/0107022 A1 | 6/2004 | Gomez |
| 2007/0164096 A1 | 7/2007 | Banfield et al. |

OTHER PUBLICATIONS

PCT International Search Report, Mailed Dec. 26, 2007, 3 Pages.

Zebra Technologies, "Adopting Bar Code Labeling in Hospital Pharmacies," Application White Paper, 2005.

W3C Working Draft, "CSSC module: Multi0 column layout", Jan. 18, 2001, 10 pages.

| Drug Data 410 |
|---|
| Drug Brand Name |
| NDC |
| DCC |
| Med Guide |
| Drug Monograph |
| Prescribing Information |
| Catalina Generated Content |
| Sponsor Generated Content |
| Med Guide Length |
| Drug Monograph Length |
| Prescribing Information Length |
| Catalina Generated Content Length |
| Sponsor Generated Content Length |
| Fill Blank Space Content |

410A (Catalina Generated Content through Sponsor Generated Content Length)

FIG. 6

| Content Selection Rules 510 |
|---|
| NDC |
| DCC |
| Switch - Med Guide |
| Switch - PI |
| Switch - Catalina Generated Content |
| Switch - Sponsor Generated Content |
| Pharmacy ID |

| Formatting Rules 520 |
|---|
| Pharmacy ID |
| NDC |
| DCC |
| Content Location Sequence |
| Switch - Wrap print |
| Switch - Fill Blank Space? |

PHARMACY PRINTER SYSTEM AND METHOD

CROSS REFERENCE TO RELATED APPLICATIONS

This application is continuation of U.S. patent application Ser. No. 13/967,286, filed on Aug. 14, 2013, which is a division of U.S. patent application Ser. No. 13/229,651, filed on Sep. 9, 2011, which is a continuation of U.S. patent application Ser. No. 11/748,239, filed May 14, 2007, which claims priority to U.S. Provisional Application Ser. No. 60/822,880 filed Aug. 18, 2006, titled "PHARMACY PRINTER SYSTEM AND METHOD". The entire contents of application Ser. Nos. 13/229,651, 11/748,239 and 60/822,880 are incorporated herein by reference.

The disclosures of the following co-owned patent applications relate to PMSs, and the disclosure of those applications are incorporated herein by reference: Ser. No. 11/366,397, filed Mar. 3, 2006, entitled "PHARMACY NETWORK COMPUTER SYSTEM AND INTEGRATED PRINTER", and PCT/US06/19432, filed May 18, 2006, entitled "SYSTEM OF PERFORMING A RETROSPECTIVE DRUG PROFILE REVIEW OF DE-IDENTIFIED PATIENTS".

The disclosure of the following co-owned patent applications relate to two sided printing to combined point of sale system register receipts and advertisements on register receipt paper, and the disclosure of those applications are incorporated herein by reference:

U.S. Provisional Application Ser. No. 60/742,908 filed Dec. 7, 2005, and U.S. patent application Ser. No. 11/488,126 filed Jul. 18, 2006, both entitled "COMBINATION PRINTER AND ITS PAPER" and these disclosures are incorporated herein by reference.

FIELD OF THE INVENTION

This invention relates to printing in pharmacies.

BACKGROUND OF THE INVENTION

U.S. Pat. Nos. 6,759,366 and 6,784,906 disclose technology enabling two sided thermal printing. Systems for printing a medicine label and related advisory information are described in U.S. Pat. No. 6,304,849 entitled "Method and system for printing a combination pharmaceutical label and directed newsletter"; U.S. Pat. No. 6,240,394 entitled "Method and apparatus for automatically generating advisory information for pharmacy patients"; and U.S. Pat. No. 6,067,524 entitled "Method and system for automatically generating advisory information for pharmacy patients along with normally transmitted data" all of which name Baxter Byerly as an inventor, and the teachings of all of which are incorporated herein by reference.

Catalina currently prints its "PatientLink" information in pharmacies. PatientLink contains information in a newsletter form including about 25% of the time sponsored information. Either Catalina or a sponsor generates the content.

Pharmacies print prescription labels. Pharmacies may also distribute additional information to prescription recipients, such as MedGuide and/or monograph. Under current practice, all MedGuide information is preprinted and shipped to each pharmacy, and the pharmacist or clerk is responsible for selecting the correct MedGuide and conveying that document with each prescription for the corresponding drug.

Many pharmacies generate their prescriptions by printing the prescription label, placing the label on a bottle, locating in their store the specified drug, placing the specified quantity of drug in the bottle, and then placing the bottle in a small bag. Then, they either staple MedGuide or related information to the bag, place that information inside the bag, or locate the preprinted MedGuide information when the prescription recipient requests possession of the prescription.

ACRONYMS

NDC is an acronym for National Drug Code.
DCC is an acronym for Drug Classification Code.
CS is used herein as an acronym for "Computer System".
CHR is an acronym for Catalina Health Resource.
POS is an acronym for Point of Sale.
FDA is an acronym for Food and Drug Administration.
CID is an acronym for Consumer IDentification.
PID is an acronym for Patient IDentification CID and PID are synonymous in this application.
XML is an acronym for Extensible Markup Language.
PMS is an acronym for Pharmacy Management System.
CS is an acronym for Computer System.

DEFINITIONS

A CID means any identifier that can be used to identify a consumer that can be scanned, read, or otherwise entered into a computer.

A "consumer" means a person or family or group of people that use the same CID when purchasing or filling a medicinal prescription in a store, such as a pharmacy store.

A POS is an area where a consumer engages in transactions with a retail store, such as a pharmacy store.

NDCs are codes associated with drugs. Preferably, NDCs are the unique 11-digit 3-segment number that identifies the labeler/vendor, product, and trade package size of a medication listed under Section 510 of the U.S. Federal Food, Drug, and Cosmetic Act.

DCCs are codes associated with medications based upon the medication's effects on human beings such that several medications may have the same DCC.

Individual transaction data includes but is not limited to data conveying some or all of following information: time of transaction, date of transaction, CID, individual transaction ID, pharmacy ID, product purchased, price of product purchases (list price and/or actual price paid), payment instrument type, payment instrument identifier.

A MedGuide is a guideline containing FDA-approved patient information associated with a DCC. For example, a MedGuide can include information such as, important information a patient should know about the drug, what the drug is, who should not take the drug or medicine, information a patient should tell a doctor before starting the drug, how a patient should take the drug, how a patient should store the drug, what a patient should avoid while taking the drug, the side effects of the drug, other information about the ailment of which the patient is taking the drugs for, the ingredients of the drug, and general information about the safe and effective use of the drug. A MedGuide contains text, which may be stored as a text computer file.

A drug monograph is a written description of a drug or medicine associated with an NDC. For example, a monograph can include information such as, introduction, summary, pharmacology, pharmaco-kinetics, FDA approved indications, off-label uses, dosage and administration, adverse effects, overdose, safety data, contraindications, warnings, precautions, drug interactions, efficacy measures, cost comparison, clinical trials, conclusions, recommendations, references, supplied, and research. A drug monograph contains text, which may be stored in a text computer file. A drug monograph is not required by the FDA. Drug monographs are third party content having drug related information. Government regulations (OBRA 1990) requires pharmacist to counsel all patients receiving Federal services. Monographs and certain other written information in practice can fulfillment the counseling requirement.

Prescribing Information (PI) or Full Prescribing Information (FPI) are documents the drug manufacturer is required to produce before a prescription drug can be sold. Patient Package Information (PPI) is a manufacturer produced document requiring FDA (government) approval, designed for the consumer, and meant to be a substitute for the PI, if approved by the FDA.

PatientLink is the name Catalina Marketing uses for the newsletter it has pharmacies print at the pharmacy store for patients receiving a prescription. PatientLink includes Catalina generated and sponsor generated content.

A PMS means a computerized system for managing pharmacy prescription information in order to assist a pharmacy in receiving and fulfilling prescriptions. It includes at least a computer including a Input/Output (I/O) terminal for a user to input pharmacy prescription information, a printer for printing prescription labels for pharmacy products, a processor for processing digital information, a memory system for storing pharmacy information, and operating system and applications programming.

Accompanying information includes but is not limited to information provided to the prescription recipient along with the prescription medicine and the prescription label. Accompanying information includes MedGuide, drug monograph, PI, FPI, PPI, and PatientLink information.

SUMMARY OF THE INVENTION

Overview

The inventors realized that current methods for providing the accompanying information originating from a variety of sources, to prescription recipients in pharmacies, is inefficient and unreliable. The inventors realized that this inefficiency is at least in part because the various types of information are printed separately in time and space.

The inventors disclose herein systems and methods for the printing in the pharmacy all information specific to a particular prescription recipient, synchronized in time with the fulfillment of the prescription. The systems and methods determine what accompanying information to associate with a prescription, integrates that accompanying information into one integrated document, and prints the document in the pharmacy prior to when the prescription recipient receives the prescription. In addition, the systems and methods determine layout of the specific accompanying information associated with a prescription to physically distinct sections of the paper.

Preferably, the systems and methods print the content on both sides of the document, preferably using a dual sided thermal printer. Preferably, the printer is a two sided thermal printer, which uses paper having a thermal barrier therein to prevent heat suitable for generating print color on one side from causing print color on the opposite side. In addition, each side of the paper may print to one color, but the colors on each side may be different; such as red/red or red/blue or red/black etc wherein the "/" indicates opposite sides of the paper.

The inventors also conceived of automated mechanisms to operate in complement with pharmacies to determine from a prescription what information content to print, and format and lay out of print for that information, for printing on two sides of paper, using a printer designed for two sided printing. The inventors conceived of structure and methods for storing all relevant information that might be printed, running rules using a prescription's information to select what specific information to print, running rules for formatting the selected information for printing, subsequently printing the formatted information, and preferably folding the paper on which printed information resides in correlation with the formatting to paginate the paper such that the print does not overlap the folds.

PMS Software Object

The system includes a PMS which includes PMS software (hereinafter the PMS Software Object, PMS SO) for assisting the pharmacy in receiving, and logging prescriptions, and fulfilling the prescriptions including printing of the prescription labels. The PMS may or may not include the hardware and software facilitating the financial transaction functions of purchasing of drugs identified in the prescriptions, often referred to as POS functions. In order to comply with data privacy law, pharmacy prescription data is not generally accessible from a POS CSs, such as a POS CS of a supermarket having a pharmacy.

The PMS SO is configured to receive prescription information entered into the PMS for request for a prescription, generate a prescription identification for the request for the prescription, log that information, and also transmit the prescription identification and at least some of the prescription information, such as a drug name or drug identification, to the Catalina Software Object (Catalina SO).

In addition, the PMS software may instruct a printer to print a prescription label (a paper having preferably the prescription drug, and perhaps dosage, and the intended recipient, on it, preferably having an adhesive backing covered by a peel away paper) for sticking on a container, such as a pill bottle, containing the prescription medicine. The prescription label may also have printed thereon a bar code readable by an optical scanner of the PMS. The bar code may encode the prescription identification. The prescription identification may be read by a scanner of the PMS. The PMS SO is configured to respond to reading the bar code by retrieving the accompanying information print file for that prescription and printing the accompanying information for that prescription. The printer has paper sized to the dimensions specified in the print file.

Catalina Software Object

The PMS includes a software object or software objects, herein after the Catalina Software Object (Catalina SO). The Catalina SO receives prescription information from the PMS SO and determines what accompanying information (as defined above) to print in association with each prescription. The Catalina SO may determine the print format of that information. The Catalina SO and the PMS SO function to generate both the prescription label and the accompanying information in printed format prior to when the prescription is delivered to the prescription recipient.

Upon receipt of prescription information, or within a short time thereafter (a short time being less time that it is likely to take for the prescription to be prepared and provided to the patient), the Catalina SO executes its rules to determine what accompanying information should be printed in response to the prescription. The Catalina SO then runs rules to determine format, that is, layout, of those items for printing on paper. Preferably, using a 2 sided printer.

Therefore, the Catalina SO determines layout for two sided printing. The Catalina SO generates a file containing accompanying information content and accompanying information layout for printing, and preferably the prescription identification. The Catalina SO will transmit this file to a print driver, which will convert it to a file for printing by a printer. Call this file the Catalina print file. Preferably, the Catalina print file is stored in association with the prescription identification. For example, a representation of the prescription identification may be embedded in the name of the print file.

The print file may contain PCL code which can be natively understood by the printer. The underlying operating system may be any variety of Unix or Windows.

Alternatively, the Catalina SO may receive sufficient prescription request information from the PMS SO to specify the contents of the prescription label, and include in the print file it generates print data for printing the prescription label. In this case, the prescription label and the accompanying information will print on the same printer, in which case preferably the printer uses a dual adhesive label and document paper form, such as referred to in U.S. Pat. No. 6,304,849.

Initial implementation of text and graphics layout will be by arranging the accompanying information in fixed areas of equal size and shape as one another, for example, two columns per page, each column being 4.4 by 8 inches wide, and 7 inches high. Each element of the accompanying information is arranged such that each items has continuity, if spanning more than one fixed column area. The code may include determination of page numbers and printing of indicia indicating continuity, such as "Continued on page 2" for a MedGuide that spans areas on pages 1 and 2.

The printer driver may print the print file or files immediately upon its or their generation. However, in most PMSs the printer drive will store the print files in association with the prescription identification in memory (typically disc memory). These print files include the prescription label print file and the accompanying information print file, or a combined prescription label and accompanying information print file.

Method of Operation

Someone, such as a patient, provides a prescription to a pharmacist, and requests that the prescription be filled.

Upon receipt of the prescription request, the pharmacist or clerk enters the prescription information into the PMS.

The PMS SO generates the prescription label

The PMS SO transmits the prescription information to the Catalina SO. For example, the PMS SO stores a file in the PMS's memory, such as disk or RAM, having a specified name or storage location. The file contains prescription information. The Catalina SO includes code to search for new files having the specified name format or stored in the specified location, and to thereafter access those files to obtain the stored prescription information.

The Catalina SO retrieves the prescription information, determines accompanying information to associated with the prescription based upon the prescription information, rules applicable to the prescription information, and stored content for accompanying information, and generates a print file containing data defining accompanying information.

Preferably, the Catalina SO causes the print file containing data defining accompanying information to print. Alternatively, the printing of the accompanying information is triggered by scanning the bar code on a prescription label for the prescription.

Next, a scanner of the PMS reads a bar code (or other machine readable indication) coding the prescription identification. The bar code preferably resides on the printed prescription label. The clerk or pharmacist retrieves the previously printed accompanying information and provides that to the patient at the same time as providing the bottle or package containing the drug to which the prescription label is affixed.

Format of Accompanying Information

The format of the printed information is important. The inventors have identified a need for a specific width range of paper of the printed information to two columns wide, each column being 4.4 inches wide. They recognized that this is dictated by the depth of existing pharmacy prescription bins; bins into which prescriptions are placed pending transfer of the fulfilled prescription to the patient. Typically, the information to be conveyed occupies more than can be printed on one piece of paper having two columns of print each column being 4.4 inches wide, and any reasonable height. Therefore, the inventors conceive of multiple pages of information being printed, and formatted via bending or binding into a multi page document. Each 4.4 inch wide by 8 inch long column of print is referred to as a panel.

Preferably, the printing is concurrent on both sides. This will provide for faster completion of printing, and time to completion is critical to avoid delaying the clerk, pharmacist, and customer/patient.

Preferably, the printing is either folded after printing, perforated, or prefolded, at distances along the direction of paper feed of 4-6 inches, such that resulting printout can be configured into booklet (folded and/or bound pages) form having a width of 4-6 inches.

The inventors envisioned the need for the multi page printing having page width of 4-6 inches and page height of about 11 inches, and prefolded paper.

In the printing and manufacturing process for dual sided thermal printing paper, paper is rolled around a drum preferably having a twenty two inch circumference/diameter. The surface of the drum contacting the paper may include protrusions or cavities resulting in lines of micro perforations in the paper at defined spacings. The micro perforations facilitate folding of the paper along the line of perforations. The drums may also have structure resulting in "end of form" marks on the paper. The "end of form" marks are indicia on the paper optically read by the printer to position paper in the printer at the start of a page for the next print job. The structure on the drum generating the micro perforations and the end of form) have to be at equi-distant points around the drum, so that sequential papers advancing around the drum are perforated at the same locations as one another, and so that paper for a subsequent print job is aligned prior to start of that print job to obtain perforation lines and end of form indicia at the intended locations. The inventors conceive of a preferred drum diameter of twenty two inches. A preferred page width is about 4.5 inches, since those page widths are commensurate with what the paper manufacturing the drum diameter can produce and will fit in conventional pharmacy prescription bins. Less preferably, the pages (and spacings between repeat patterns of structure of the surface of the drum forming micro perforations) may be four to six inches in width. A preferred page height is 8 inches.

The inventors recognized that a problem with providing the desired information is regulatory compliance. The regulatory required accompanying information is provided for less than half of all prescriptions. The system and methods disclosed herein should increase compliance by easing the burden of the pharmacist in associating the correct informational papers with each prescription. However, the pharmacist or clerk would still have to physically associate printed material with the fulfilled prescription prior to providing the prescription to the prescription recipient.

In one alternative, the printer of the accompanying information is designed to print that information paper pre formed into bags. The indicia printed on the bag preferably includes a unique identification of the prescription, such as a representation of the prescription identification (bar code, number, etc). That enables the pharmacist or the patient to visually associate the prescription label with the printed bag for that prescription. This embodiment ensures a higher level of compliance with regulatory requirements. Optionally, the printer prints non bag paper, and that printed paper is post processed, either by hardware attached to the printer or a separate device, to form a bag.

In other embodiments, hardware attached to the printer bends and/or binds the pages of the printed accompanying information and/or binds the printed accompanying information into a pamphlet or a book format.

Catalina SO Content Switches

The Catalina SO stores, by drug identification and retail store identification, which MedGuides and other accompanying information to include in the print jobs for prescriptions specifying each drug, whether to print on refills of a prescription, the MedGuides and the other accompanying information. These options regarding what to print based upon drug identification in a prescription and retail store identification are sometimes referred to as software switches. These options may be stored in a table including fields for drug identification, retail store identification, whether to print MedGuide, whether to print other accompanying information, whether to print MedGuide on refill, whether to print other accompanying information upon refill. For example, for a particular drug, drug X, the Catalina SO in the PMS in one retail store (or more likely in the PMSs of all retail stores owned by the same company) might be programmed to print no accompanying information, or no MedGuide.

In addition, that PMS might be configured to not print MedGuides for refills on a prescription, or not print refills on a prescription for drug X, but print MedGuides for refills for drug Y. The PMS would need to pass the prescription refill status information to the Catalina SO, so that the Catalina SO could make those determinations for each prescription.

Interaction with a Central CS

In addition, the Catalina SO may be programmed to transmit the prescription information received by the Catalina SO out of the PMS to a central CS. The central CS may be configured to transmit data from the central CS back to the PMS for the Catalina SO. This data may include instructions resulting from the central CS processing of the prescription information. The transmissions to and from the central CS would be prompt, on the order of less than seconds or minutes, so that the PMS could act on instructions prior to when the clerk or pharmacist in the corresponding pharmacy fulfills the corresponding prescription. For example the central CS could run code specifying what sponsored material to include in the printed accompanying information, and transmit the sponsored material to the PMS for inclusion in the print file for printing the accompanying information. In addition, the central CS could then agglomerate prescription drug purchase information across a large number of pharmacy stores to rapidly determine, for example, changes in with time in drug purchasing for each drug, to provide a quick indication of sales to the drug manufacturers. Drug manufactures might use that information in conjunction with the timing of regional or national advertising campaigns, to determine the effectiveness of that advertising, and to determine when to produce more or less of a specified drug, thereby controlling drug inventory. Preferably, the central CS stores in memory a geographic region in association with the identification of each PMS pharmacy. However, data received at the central CS originating in a PMS may include some indicia indicating the physical location of the corresponding pharmacy. For example, a network identification otherwise associated with a geographic region.

Central CS Services

The central CS transmits all updates to accompanying information to each PMS. In addition, the central CS may transmit update of formatting and content selection rules for accompanying information to each PMS.

The central CS preferably provides a related service. The central CS queries, prompts, or otherwise obtains via download from each one of a plurality of drug manufacturer's networked CSs, MedGuide data, reformats the MedGuide data, and downloads the reformatted MedGuide data to either (1) a Catalina CS or printer database in each of a plurality of pharmacies or (2) to the PMS for each of those pharmacies, or some of each. The central CS obtains, via manual or automated monitoring, identifications of drugs going off patent, and manually or automatically derives from the drug class information generic MedGuides for generic versions of the same drug. The derivation removes the trademarked name of the drug, and clarifies the source of any study results specified in the new MedGuide. For example, indicating that study results are industry studies, and for example specifying the manufacture that sponsored the studies, and otherwise comply with MedGuide formatting as to letter sizes heading sizes, and white space requirements. The central CS can transmit revised and new MedGuides to each PMS, in the central CS's specified format.

Prescription Data Received by the Catalina SO

Currently contemplated fields for the data the Catalina SO receives from the pharmacy computer system software (PMSS) in the data record include (from Catalina Health Resource XML Interface Overview, Version 3.0, rev. 6): XML Header; Message version; State Code; Region; Retailer division; Retailer Store; NCPDP ID Number; Language Indicator; Unique Patient ID; Customer Name; Name Mask; Date of Birth; Gender; Opt Out (HIPAA); Transaction Sequence; Script Status; NDC; Medication Name; RX Number; Dispensed Qty.; Refill Sequence; Daily Supply qty; Daily Supply days; Original Fill Date; Expires Date; Refills Remaining; Monograph; Patient Directions; Pharmacist Directions; Dr Number; Simplex or Integrated; HIPAA Privacy msg; Payor; Payor Code; Control Number; Bin Number; Agency; Group; and Plan.

Prescription Data Received by the Catalina SO

Currently contemplated fields for the data the Catalina SO receives from the pharmacy computer system software (PMSS) in the data record include (from Catalina Health Resource XML Interface Overview, Version 3.0, rev. 6): XML Header; Message version; State Code; Region; Retailer division; Retailer Store; NCPDP ID Number; Language Indicator; Unique Patient ID; Customer Name; Name Mask; Date of Birth; Gender; Opt Out (HIPAA); Transaction Sequence; Script Status; NDC; Medication Name; RX Number; Dispensed Qty.; Refill Sequence; Daily Supply qty; Daily Supply days; Original Fill Date; Expires Date; Refills Remaining; Monograph; Patient Directions; Pharmacist Directions; Dr Number; Simplex or Integrated; HIPAA Privacy msg; Payor; Payor Code; Control Number; Bin Number; Agency; Group; and Plan.

FORMAT: Field; Format (example); Description; Start tag; End Tag

XML Header; Alpha-text; XML header tag; <?XML version="1.0"?>; N/A Message identifier; Alpha-text; XML tag; <newsletter>; </newsletter>

Message version; Alpha-text Version (3.0); Message version number; <MessageVersion>; </MessageVersion>

State Code; Alpha-text (2); State code for store location; <StateCode>; </StateCode> Region;

Numeric text, variable length (4); Geographic region; <DMAD>; </DMAD>

Retailer division; Alpha-numeric text (10); Division id to aid in triggering division specific programs; <Division>; </Division>

Retailer Store; Alpha-numeric text (4); Store id to aid in triggering store specific programs; <Store>; </Store>

NCPDP ID Number; Alpha Numeric (7); National Council for Prescription Provider ID.; <NCPDP>; </NCPDP>

Language Indicator; Alpha-text, 1 char E or S (S); English or Spanish language preference.; <Language>; </Language>

Unique Patient ID; Alpha-numeric variable length text (123456A); Pharmacy system's unique patient identifier.; <PatientId>; </PatientId>

Customer Name; Alpha-numeric variable length text (Jane Doe); Patient name is required to personalize the newsletter.; <PatientName>; </PatientName>

Name Mask; Alpha-numeric variable length text (Y); A flag to tell our software to mask patient name with "Valued Customer"; <MaskName>; </MaskName>

Date of Birth; Alpha-numeric text, 10 chars mm/dd/yyyy (02/06/1962); Used to calculate the patient's age.; <DateOfBirth>; </DateOf Birth>

Gender; Alpha text, 1 char M or F or U (M); M—Male F—FemaleU—unknown; <Gender>; </Gender>

Opt Out (HIPAA); Alpha-numeric variable length text (Y); A flag to tell our software this patient does not want his/her information used to trigger a newsletter. And does not want to receive a newsletter; <OptOut>; </OptOut>

Transaction Sequence; Numeric text (15); Transaction number from RX system, used for QA purposes; <TransSeq>; </TransSeq>

Script Status; Alpha text, 1 char N or R (R); N—New ScriptR—Refill; <ScriptStatus>; </ScriptStatus>

NDC; Numeric text, 11 digit ########### (12345678901) or alpha-numeric, 13 chars#####-####-## (12345-6789-01); 11 digit National Drug Code (with or without standard dashes); <NDC>; </NDC>

Medication Name; Alpha-numeric variable length text (Zocor); This information is printed on the newsletter. May contain actual drug name and phonetic spelling.; <MedicationName>; </MedicationName>

RX Number; Alpha-numeric variable length text (123456A); Prescription number is printed on the newsletter. Used for message validation.; <rxNumber>; </rxNumber>

Dispensed Qty.; Numeric text (25); Qty of medication dispensed, i.e. pill count; <DispQty>; </DispQty>

Refill Sequence; Numeric text (2); Field contains 0 for new scripts. On the first refill this field would contain 1.; <RefillNumber>; </RefillNumber>

Daily Supply qty; Numeric, variable length (3); Daily qty of consumption of medication. i.e. 3 pills; <DailySupply>; </DailySupply>

Days Supply days; Numeric, variable length (30); Number of days this script is intended to last.; <DaysSupply>; </DaysSupply>

Original Fill Date; Alpha-numeric text, 10 chars mm/dd/yyyy (02/06/2000); This is the date that the prescription originally got filled as a new script.; <FillDate>; </FillDate>

Expires Date; Alpha-numeric text, 10 chars mm/dd/yyyy 02/06/2001); This is the date that the original prescription expires.; <ExpireDate>; </ExpireDate>

Refills Remaining; Numeric text, variable length (3); Total refills less the ones that have already been filled.; <Remaining>; </Remaining>

Monograph; Alpha-numeric variable length text (123456A); Monograph to be printed on the newsletter.; <Monograph>; </Monograph>

Patient Directions; Alpha-numeric variable length text (123456A); Patient directions to be printed on the newsletter.; <Directions>; </Directions>

Pharmacist Directions; Alpha-numeric variable length text 123456A); Pharmacist directions to be printed on the newsletter.; <RxDirections>; </RxDirections>

Dr Number; Alpha-numeric variable length text (123456A); Dr.'s identification number.; <DrId>; </DrId>

Simplex or Integrated; Boolean value; A flag to tell our software whether the newsletter will be integrated with the label or not (separate from the label—simplex).; <IntegrateNewsletter>; </IntegrateNewsletter>

HIPAA Privacy msg; Y/N (1); Y=do not print msg, N=print msg.; <HIPAA>; </HIPAA>

Payor; Alpha-numeric variable length text (CASH); Third party payer name/description. CASH if customer paid.; <Payor>; </Payor>

Payor Code; Alpha-numeric variable length text (CASH); Third party payer code CASH if customer paid.; <PayorCode>; </PayorCode>

Control Number; Alpha Numeric (9); Payer's processor control number.; <ControlNumber>; </ControlNumber>

Bin Number; Numeric (6); Bank Identification Number. Payer code information.; <BinNumber>; </BinNumber>

Agency; Alpha-numeric variable length text (123456A); The legal relationship between an agent and a principal; <Agency>; </Agency>

Group; Alpha-numeric variable length text (123456A); Insurance that provides coverage for several people under one contract, called a master contract.; <Group>; </Group>

Plan; Alpha-numeric variable length text (123456A); A plan document identifies the benefits the participants are to receive and the requirements they must meet to become entitled to those benefits.; <Plan>; </Plan>.

Additional concepts include the following.

Providing in print a change of color, contrast, other highlighting, or a particular logo, when printed accompanying information includes recently updated information, such as information on newly identified side effects. This would alert patients to changes in information about the medicine they were taking.

Adding disposable/programmable audio device—chip as an alternative or in addition to medGuide/PI printed information; possibly integrated into a pill bottle. Add telephone service providing recorded message of med guide/monograph info. One telephone number per prescription type, and one such telephone number on each bottle label. Provide corresponding dial up service, and integrate number/prescription type print into the software code printing the prescription and/or printing the accompanying information.

DETAILED DESCRIPTION OF THE EMBODIMENTS

Figure 1:
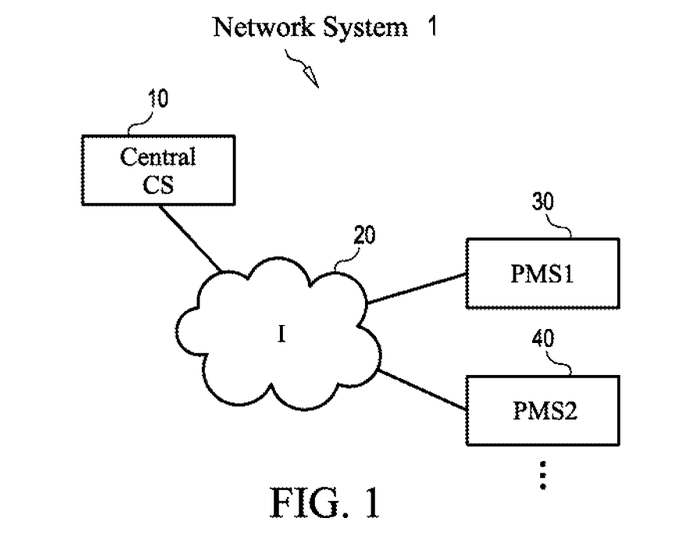
FIG. 1 is a schematic of computer network 1.

FIG. 1 shows a computer network including a central CS 10, and a series of PMSs including PMS1 30, PMS2 40, etc, connected via a wide area network 20, such as the Internet.

Lines shown connecting elements represent conventional network packet switched or always connected data communication lines. Each computer includes a central processing unit for processing instructions, memory, and input/output devices for interacting with human beings. Each PMS controls the prescription fulfillment process at one or more pharmacies.

Figure 2:
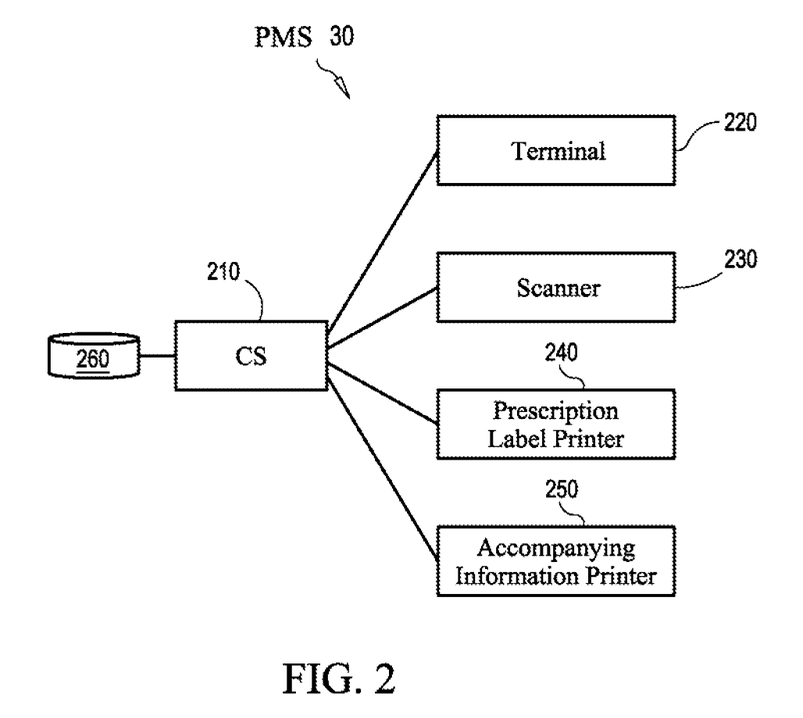
FIG. 2 is a schematic of PMS 30 of FIG. 1.

FIG. 2 show PMS 30 including CS 210, memory or database 260, read and write access to which is controlled by CS 210, terminal 220, for input and output of data, scanner 230, for input of data in the form of optically recognizable bar codes, prescription label printer 240 for printing inter alia prescription labels and bar codes, and accompanying information printer 250 for printing inter alia accompanying information. Alternatively, any or each of the elements 220-250 may comprise a CS networked via a local area network to CS 210. In one alternative, accompanying information printer 250 stores all text and graphical accompanying information, and it receives from CS210 reference to elements of that information indicating to printer 250 what accompanying information to print in association with a specified prescription. More details on such an alternative exists in U.S. application 60/759,552, filed Jan. 18, 2006, and U.S. application Ser. No. 11/366,397, filed Mar. 3, 2006, both entitled "PHARMACY NETWORK COMPUTER SYSTEM AND INTEGRATED PRINTER" and both of which are hereby incorporated by reference.

Figure 3:
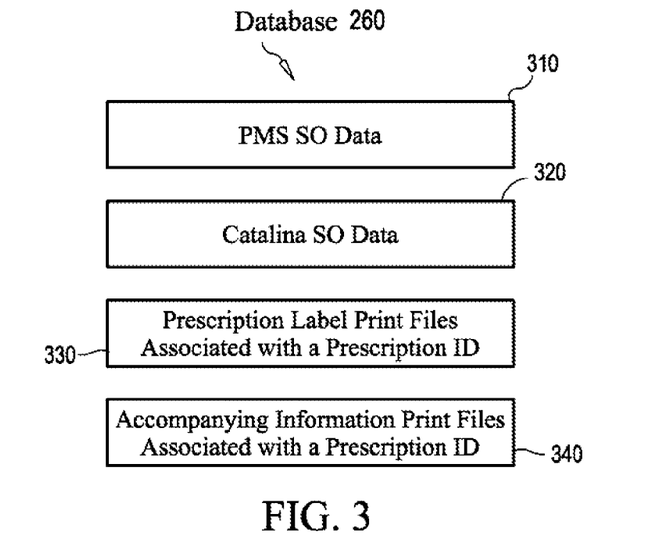
FIG. 3 is a container schematic of database 260 of FIG. 2.

FIG. 3 shows contents of database 260 including PMS SO data 310, Catalina SO data 320, prescription label print files 330, each associated with a prescription ID, and accompanying information print files 340, each associated with a prescription ID. Files 330, 340, are the files ready for printing the prescription labels and accompanying information associated with specified prescription identifications.

Figure 4:
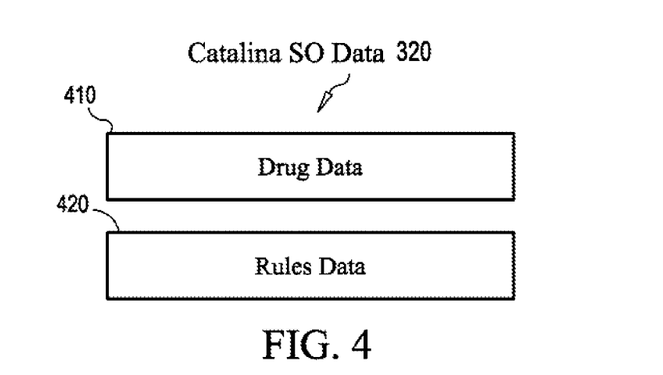
FIG. 4 is a container schematic of Catalina SO data 320 of FIG. 3.

FIG. 4 shows contents of the Catalina SO data including drug data 410 and rules data 420. Drug data 410 includes all accompanying information for each identified drug product. Rules data 420 includes rules determining what accompanying information content to print for a prescription, and how to format that content for printing.

Figure 5:
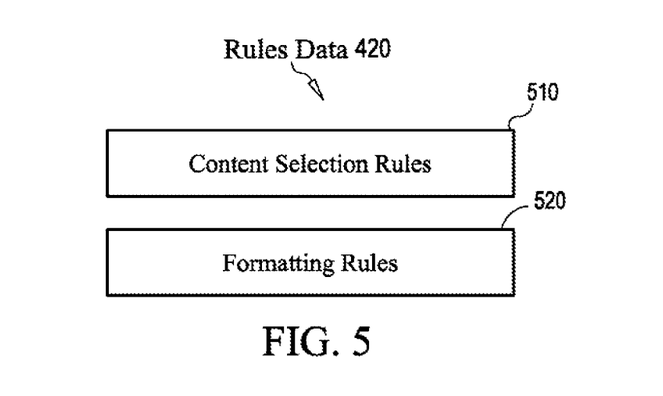
FIG. 5 is a container schematic of rules data 420 of FIG. 4.

FIG. 5 shows rules data 420 including content selection rules 510 and print formatting rules 520.

Figure 6:
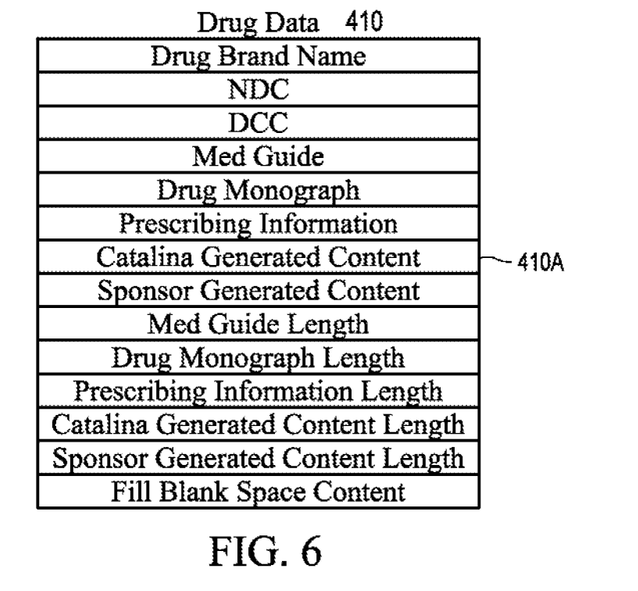
FIG. 6 is a design view of drug data table 410A for drug data fields of drug data 410 of FIG. 4.

FIG. 6 shows a design view of table 410A storing fields for drug data 410. FIG. 6 shows fields with names representing the data stored in the field. The field names are drug brand name, NDC, DCC, MedGuide, monograph, prescribing information, Catalina generated content, Sponsor generated content, MedGuide length, monograph length, prescribing information length, Catalina generated content length, sponsor generated content length, and fill blank space content. The field names are only exemplary in that for example, there may be additional fields for additional sponsored content, and additional field for the various different types of prescribing information. The "length" fields contain a measure of print length for text content, such as character count or line count. The length fields may be used by formatting rules as specified below.

Alternatively, the field for potentially repetitive content, repetitive over more than one drug product such as MedGuide, monograph, prescribing information, and generated content, may be stored in a separate table and identified in table 410A only by a reference therein to the other table, for example using a foreign key.

Moreover, the drug data 410 may in fact be stored in a database in the printer that prints the accompanying information. In this embodiment, the drug data stored in database 260 (database controlled by CS 210), may only store a reference to the data fields for the MedGuide, monograph, prescribing information, etc, such a reference for example being the DCC and/or NDC. In this embodiment, the processor in the printer may perform the content and format determinations noted above as performed by the Catalina SO.

Figure 7:
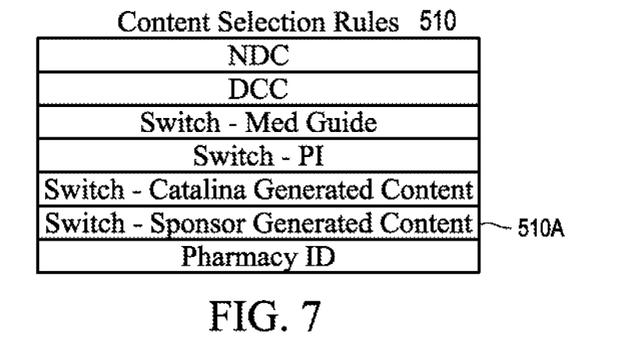
FIG. 7 is a design view of content selection rules table 510A for content selection rules data 510.

FIG. 7 shows a design view of table 510A representing content selecting rules 510. This is only one of alternative ways to represent content selection rules. In this representation, table 510A includes field names wherein the field names describe the content, and those field names are: NDC, DDC, Switch—MedGuide; Switch—PI; Switch—Catalina generated content; Switch—Sponsor generated content; and Pharmacy or PMS ID. The "Switch" fields are boolean fields indicating whether to print the corresponding accompanying information: MedGuide, PI, and generated contents.

Figure 8:
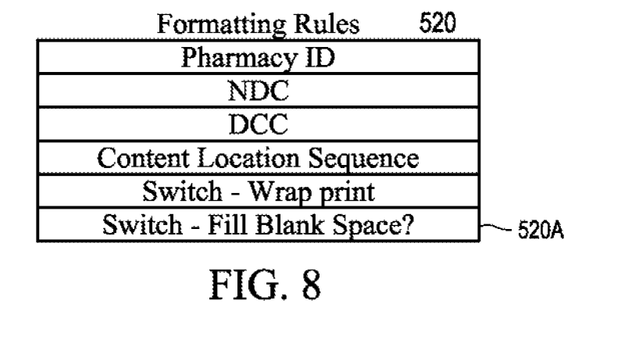
FIG. 8 is a design view of formatting rules table 520A for formatting rules data 520.

FIG. 8 shows a design view of table 520A having fields for storing formatting rules 520. In this representation, table 520A includes field names wherein the field names describe the content, and those field names are: Pharmacy (or PMS) ID; NDC; DDC; Content location sequence; Switch—Wrap Print; and Switch—Fill Blank Space. The content location sequence contains datum indicating sequence of print of the various identified components of accompanying information, such as MedGuide, then Monograph, then Catalina Generated content. As a result, these elements of accompanying content would print with MedGuide starting on page 1, and the other elements following on sequential from where the MedGuide print ended.

Print text and graphics are laid out in "plates" which correspond to the height and width of a column of text to appear on a printed page. For example, there may be 1, 2, or 3 printed columns.

The Switch—Wrap Print is a value determining where to begin printing a subsequent element of accompanying data, such as monograph, after end of print of a prior element, such as MedGuide. For example, printing of the monograph may begin on the next line after the last line of the MedGuide in the same column in which the MedGuide print ends, in the sequentially next column after the end of the MedGuide, or on the sequentially next page after then end of the MedGuide.

Switch—Fill Blank Space contains one or more values indicating how the Catalina SO should fill any blank space. Blank space is space resulting from unfilled rows or pages due to the values for Switch—Wrap Print and whether there exists blank space on the last page of the printed document.

Figure 9:
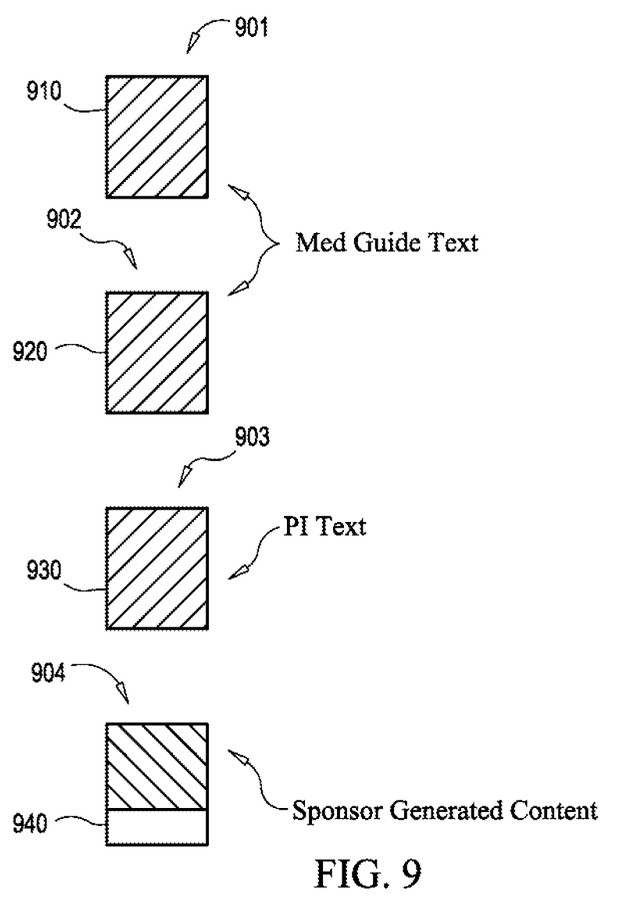
FIG. 9 shows simplified plan view of accompanying data laid out on plates of printed page size.

FIG. 9 shows plates 901-904 (height and width each corresponding to a column for text printing) and printed material thereon indicated by hashing. Plates 901 and 902 have print 910 and 920 indicating MedGuide text/graphics. Plate 903 has print 930 indicating PI text/graphics. Plate 904 has print 940 indicating sponsor generated content. Plates 901-904 are each shown having a single column of text for simplicity of illustration.

Figure 10:
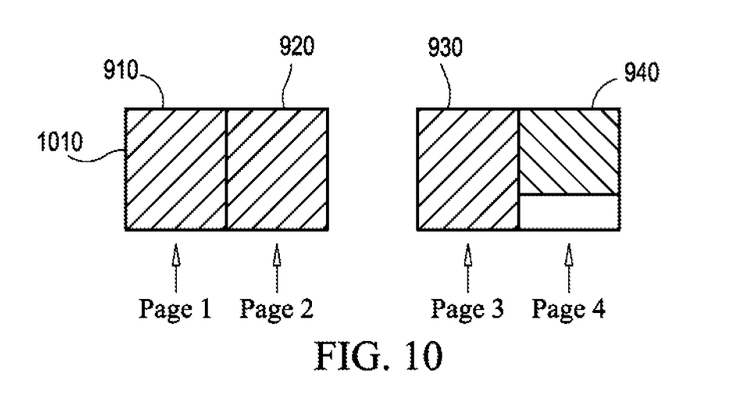
FIG. 10 shows front and back plan views of a first alternative format for printing of accompanying information shown in FIG. 9.

FIG. 10 shows a front side 1010 and a back side 1020 of a paper having the information shown in FIG. 9 printed thereon. FIG. 10 shows each type of information, MedGuide, PI, and Monograph, starting on a distinct page/column of paper, corresponding to a value of Switch Wrap Print, indicating print for each element of accompanying information starting on a new page or column.

Figure 11:
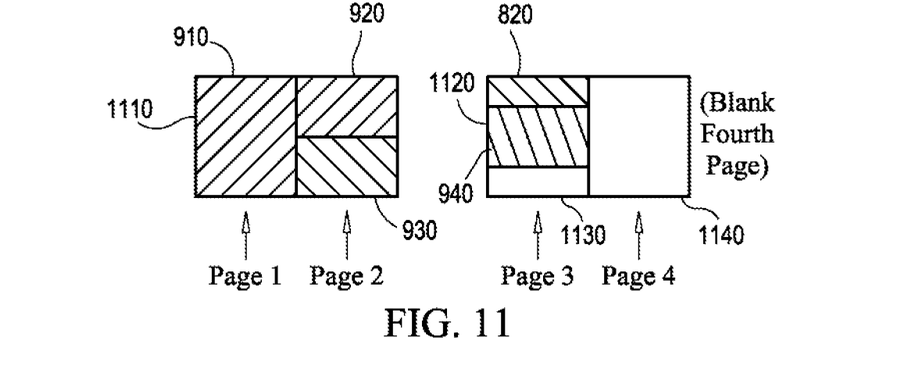
FIG. 11 shows front and back plan views of a second alternative format for printing of accompanying information shown in FIG. 9.

FIG. 11 shows a front side 1110 and a back side 1120 of a paper having the information shown in FIG. 9 printed thereon. FIG. 11 shows printing in which Switch Wrap Print indicates printing of accompanying information continues in the same column after one element of accompanying information ends. As a result, an unprinted region exists at the bottom of page 3, and there is no print on page 4. Switch—Fill blank space determines whether the Catalina SO retrieves additional information to fill the blank space. The additional information for filling blank space may be PMS specific information, such as PMS advertising, PMS incentive offers, manufacturer sponsored incentive offers, or other informational materials. This information may be stored in the PMS in a location and in a format accessible to the Catalina SO.

Figure 12:
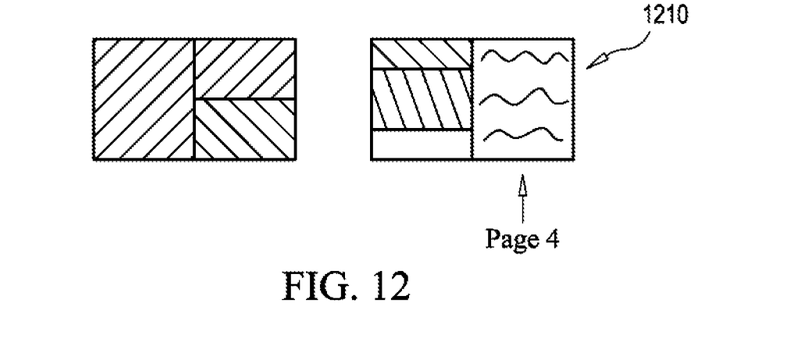
FIG. 12 shows front and back plan views of a third alternative format for printing of accompanying information shown in FIG. 9 that includes printing fill data.

FIG. 12 shows the same information as FIG. 11, except that it includes on page 4 fill content 1210.

Figure 13:
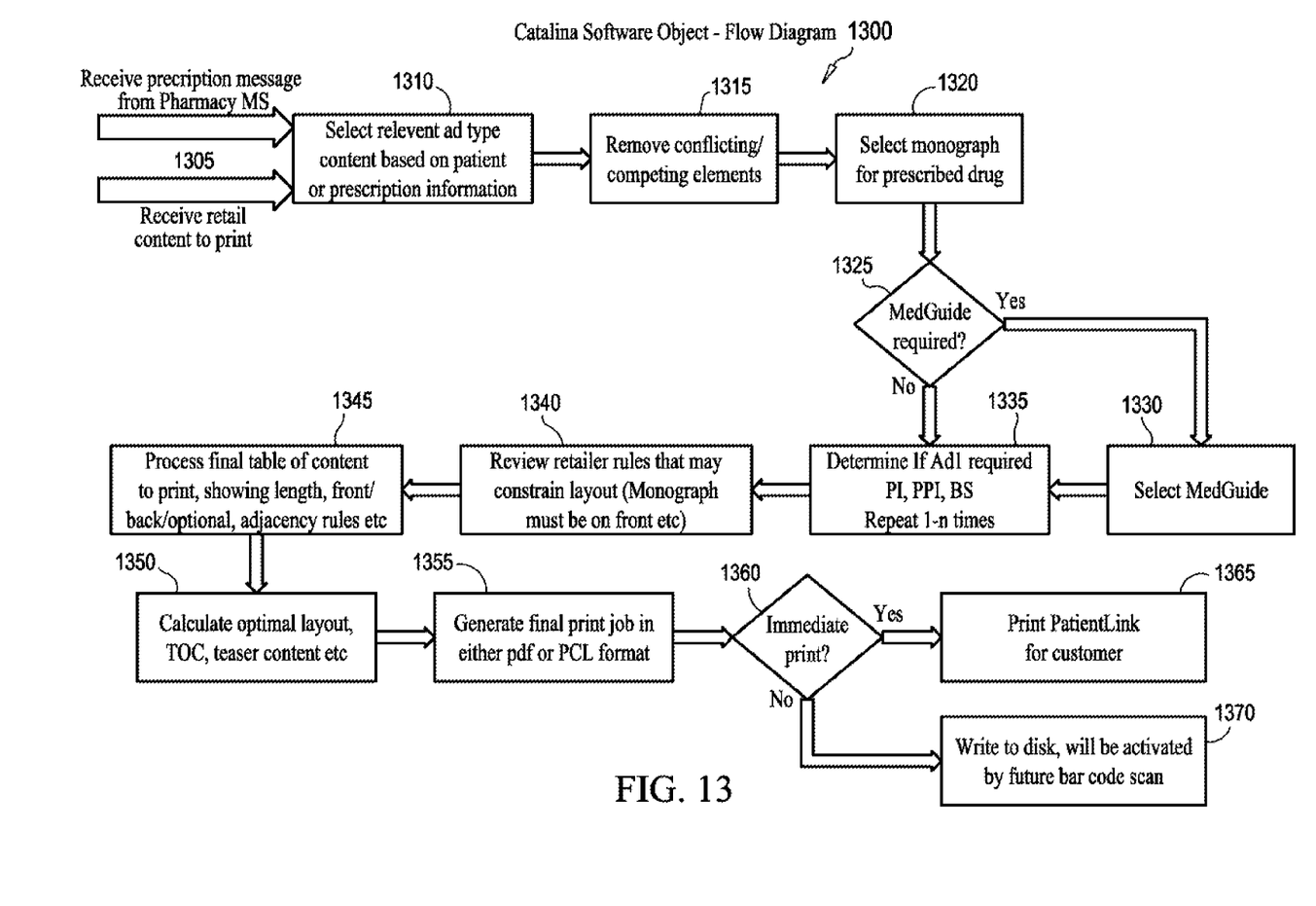
FIG. 13 is a schematic process flow diagram for the Catalina SO.

FIG. 13 shows the process flow 1300 for a preferred embodiment of the Catalina SO. In step 1305, the Catalina SO receives a prescription message from the PMS SO and optional retailer content to print. As to the retailer content, this is information that the retailer specifies for the Catalina SO to configure and print. For example, a particular retailer may desire to have their versions of drug monographs printed. In that case, their PMS SO would send data defining their drug monograph to the Catalina SO.

In step 1310, the Catalina SO selects additional content based upon patient or prescription information. Note that in step 1305 the prescription message may include Unique Patient ID. The patient ID may be used to trigger print of patient ID specific information. This information may have previously been stored locally in the PMS. This information may have been associated with the patient ID at a central CS and thereafter transmitted to the PMS, for the Catalina SO.

In step 1315, the Catalina SO removes any competing elements. For example, when the retailer sends a drug monograph and the Catalina SO determines another drug monograph for the same drug.

In step 1320, the Catalina SO selects the drug monograph for the prescribed drug.

In step 1325, the Catalina SO determines whether to print a MedGuide. If yes, it proceeds to step 1330. If no, it proceeds to step 1335.

In step 1330, the Catalina SO selects a MedGuide for printing.

In step 1335, the Catalina SO determines if Ad1 is required, PI, PPI, BS, and repeats this process n times. Ad1 means advertisement number 1. Pi means perscribing information, which is a document produced by drug manufacturers and intended for us by doctors as aid in prescribing and accompanies medicine shipped to pharmacies. PPI means patient product information designed for patients. BS means brief summary and is a brief summary of the PI. In operation, in step 1335, advertisements for prescription drugs are associated with at least one of a corresponding PI, PPI, BS for that drug. The process of determining print information repeats for each prescription drug advertisement to be printed, hence, n times for n such advertisements.

In step 1340, the Catalina SO reviews and implements retailer specific rules regarding layout, such as a rule requiring the drug monograph be on the front page of the print.

In step 1345, the Catalina SO processes a final table of content to print.

In step 1350, the Catalina SO determines optimal layout of print elements, determines the TOC, and layout of any teaser content.

In step 1355, the Catalina SO generates the final print job in either pdf or PCL format.

In step 1360, the Catalina SO determines whether or not to print immediately. If yes, proceed to step 1365. If no, proceed to step 1370.

In step 1365, the Catalina SO sends the print job to the printer, which prints the print job for the customer.

In step 1370, the Catalina SO writes to disk or memory the print job.

In an additional step related to step 1370, the prescription ID is scanned, which triggers printing of the print job. In practice, this is usually when the pharmacist is assembling the prescription drugs in a package, so that the pharmacist can then affix the printed information to the corresponding prescription drug package. Alternatively, the print job may be triggered by scanning the prescription ID at the time the customer picks up the drub package, and at that time also provided to the customer along with the prescription drug package.

What is claimed is:

1. A method of processing accompanying information related to a prescription, the method being implemented on a computing device having a processor programmed by one or more computer program instructions, the method comprising:
    determining a layout used to print accompanying information for a prescription request, the layout comprises an indication of a number of columns to be printed per page and the accompanying information is based on prescription information and comprises two or more elements;
    determining print indicia that indicates continuity data for at least one of the two or more elements that spans more than one column;
    generating a print file used to print the accompanying information based on the layout, the print file including the determined print indicia; and
    printing the accompanying information using the print file.

2. The method of claim 1, further comprising:
    transmitting the prescription information to a server;
    receiving accompanying information from the server; and
    receiving sponsored content from the server.

3. The method of claim 2, wherein the determining the layout comprises:
    determining a layout for printing the accompanying information and the sponsored content.

4. The method of claim 1, wherein the determining the layout comprises:
    applying a rule for at least one of selecting content or formatting content.

5. The method of claim 4, further comprising:
    receiving from a server an update for at least one of a content selection rule or a content formatting rule.

6. The method of claim 5, wherein the content selection rule or the content formatting rule is provided by a retailer operating a pharmacy management system.

7. The method of claim 1, wherein the generating a print file further comprises:
generating a print file based on the layout.

8. The method of claim 1, further comprising:
determining the layout comprises an unprinted region; and
inserting additional information in the layout to fill the unprinted region.

9. The method of claim 1, further comprising:
storing the print file in association with the prescription request, the prescription request comprises an associated bar code.

10. The method of claim 9, further comprising:
printing the print file using a printer when the printer is presented with the associated bar code.

11. A method of processing accompanying information related to a prescription, the method being implemented on a computing device having a processor programmed by one or more computer program instructions, the method comprising:
determining, by the processor, accompanying information to be printed for a prescription request, the accompanying information is based on prescription information and includes a plurality of elements; determining, by the processor, a layout used to print the accompanying information, wherein the layout comprises a plurality of columns to be printed per page, and wherein the determining the layout comprises formatting a first element to be printed on a first column and a second element to be printed;
generating, by the processor, a print file used to print the accompanying information based on the layout; and
printing the accompanying information using the print file.

12. The method of claim 11, wherein the determining the layout further comprises:
formatting at least a first portion of the second element to be printed in the first column.

13. The method of claim 12, further comprising:
formatting at least a second portion of the second element to be printed in a second column.

14. The method of claim 13, further comprising:
determining the second column comprises an unprinted region; and
inserting additional information into the unprinted region.

15. The method of claim 14, further comprising:
determining a second layout rule provided by a retailer; and
prioritizing the second layout rule from the retailer as a higher priority than the first layout rule to determine the layout.

16. A device for processing accompanying information related to a prescription, the device comprising:
a processor programmed with one or more computer program instructions to:
determine accompanying information to be printed for a prescription request having an associated bar code, the accompanying information is based on prescription information in the prescription request and includes a plurality of elements; determine a layout used to print the accompanying information, wherein the layout comprises a number of columns to be printed per page; format a first element of the plurality of elements and a first portion of a second element of the plurality of elements to be printed in a first column; format at least a second portion of the second element to be printed in a second column different from the first column; format additional information to fill the second column based on a determination that the second column comprises an unprinted region;
generate a print file used to print the accompanying information based on the layout and wherein the processor further programmed to: cause a printer to print the print file using paper having a size that is defined by a layout rule.

17. The device of claim 16, the processor further programmed to:
store the print file in association with the prescription request.

18. The device of claim 16, wherein the printer prints the print file upon being presented with the associated bar code.

* * * * *